United States Patent [19]

Sheridan

[11] Patent Number: 4,578,170

[45] Date of Patent: Mar. 25, 1986

[54] MOUNTING STRUCTURE FOR ELECTRONIC PROBES

[75] Inventor: Michael Sheridan, Old Bridge, N.J.

[73] Assignee: Ethylene Corp., Murray Hill, N.J.

[21] Appl. No.: 720,495

[22] Filed: Apr. 5, 1985

[51] Int. Cl.[4] ............................................. G01N 27/30
[52] U.S. Cl. ................................. 204/400; 251/149.6; 324/447
[58] Field of Search ............... 204/400, 404, 403, 412, 204/414, 415, 416, 417, 418, 419, 420, 433; 324/425, 438, 450, 446, 447, 448, 449; 251/149.6, 149.7

[56] References Cited

U.S. PATENT DOCUMENTS

| | | | |
|---|---|---|---|
| 2,830,260 | 4/1958 | Del Chiocca | 324/446 |
| 2,830,261 | 4/1958 | Estelle | 324/446 |
| 2,832,039 | 4/1958 | Hardesty | 324/450 |
| 2,884,365 | 4/1959 | De Bolt et al. | 204/195 |
| 2,985,821 | 5/1961 | Del Chiocca | 324/450 |
| 3,166,485 | 1/1965 | Lloyd | 204/400 X |
| 3,352,531 | 11/1967 | Kilmarx | 251/149.6 |
| 3,399,677 | 9/1968 | Gould et al. | 251/149.6 X |
| 3,538,950 | 11/1970 | Porteners | 251/149.6 X |
| 3,718,567 | 2/1973 | Haddad et al. | 204/195 P |
| 3,806,440 | 4/1974 | Gray et al. | 204/195 G |
| 4,008,141 | 2/1977 | Kotani et al. | 204/195 G |
| 4,166,020 | 8/1979 | Trampert | 204/195 R |
| 4,320,343 | 3/1982 | Ingram | 324/450 |
| 4,383,908 | 5/1983 | Phelps et al. | 204/409 |
| 4,447,309 | 5/1984 | Morioka et al. | 204/402 |

FOREIGN PATENT DOCUMENTS 2062010 12/1971 Fed. Rep. of Germany ...... 324/446

OTHER PUBLICATIONS

Pfaudler pH Measuring System Bulletin 1132.
De Dietrich pH Probe Brochure, 1984.

Primary Examiner—G. L. Kaplan
Attorney, Agent, or Firm—Charles E. Temko

[57] ABSTRACT

A rapidly demountable structure for supporting electronic probes within a reactor vessel at the inner end of a dip tube element. The structure includes a fixed dip tube element which is permanently positioned in a recess at the inner end of the dip tube, and a probe supporting element selectively engaged with the dip tube element through a bayonet type interconnection. A damaged probe is replaced by first disconnecting the probe supporting element from the dip tube element, and disassembling the probe supporting element to permit removal and replacement of the probe. Means is provided to seal the opening to the reactor vessel during the period in which the probe supporting element is in disengaged condition thus affording safety to service personnel during replacement of the damaged probe.

1 Claim, 3 Drawing Figures

MOUNTING STRUCTURE FOR ELECTRONIC PROBES

BACKGROUND OF THE INVENTION

This invention relates generally to the field of chemical processes using reactor vessels, and more particularly to an improved means for supporting electronic sensing probes such as pH probes and the like.

In the processing of many chemical products, it is often desirable if not essential, to continuously monitor such variables as temperature, pH value, and similar characteristics. To fulfill this need, it is known in the art to provide electronic probes which are continuously immersed in the reactants, normally being introduced and supported by one of the smaller openings in the reactor vessel which are also used to support dip tubes or spargers.

In the case of pH measurement, while the entire probe assembly is relatively expensive, and correspondingly durable, the active electrode which is located at the end of the probe is carried within a glass filled tip which continuously deteriorates as it releases ions into an electrolyte necessary for operation of the probe. Accordingly, it must be replaced when it is no longer responsive. In the past, this has necessitated removal of the probe element and substantial disassembly thereof to replace the tip electrode. When electrode failure occurs during the processing of a batch of material, it is necessary to either interrupt the operation of the reactor, while replacing the electrode, or to continue the processing without the benefit of monitoring, an undesirable course in either event. If the electrode is replaced during processing, the removal of the probe leaves an opening leading to the reacting mass with the possibility of splattering of the same upon nearby service personnel, and possible accompanying injury.

SUMMARY OF THE INVENTION

Briefly stated, the invention contemplates the provision of an improved mounting structure for electronic probes incorporated into the end of a specialized dip tube penetrating a reactor vessel which allows the immediate withdrawal of the electronic probe for replacement, thus eliminating the need for shutting down the processing of a reacting batch of material then in process. The improved structure includes a fixed mounting element permanently secured within a dip tube opening and forming a slotted bayonet type socket. A probe carrying element is selectively engaged within the socket to thereby position the end of one or more probes within the reactor vessel so that the operative end of the probe will be disposed in the reacting mixture. The probe carrying element is readily disassembled when disengaged from the fixed mounting element to permit removal of the probe to be replaced by a new probe, or the electrode on the existing probe may be replaced, following which the probe carrying element is again reassembled to be again positioned within the fixed mounting element. If desired, a complete spare assembly of probe and probe carrying element may be maintained in stock, so that the entire replacement process may require momentary interruption of operation of the reactor vessel. Means is provided for the automatic closing of the opening leading to the vessel during the period in which the probe carrying element is removed to prevent accidental splattering of the reacting contents of the vessel outwardly of the dip tube opening with possible injury to personnel.

BRIEF DESCRIPTION OF THE DRAWING

In the drawings, to which reference will be made in the specification, similar reference characters have been employed to designate corresponding parts throughout the several views.

DETAILED DESCRIPTION OF THE DISCLOSED EMBODIMENT

Figure 1:
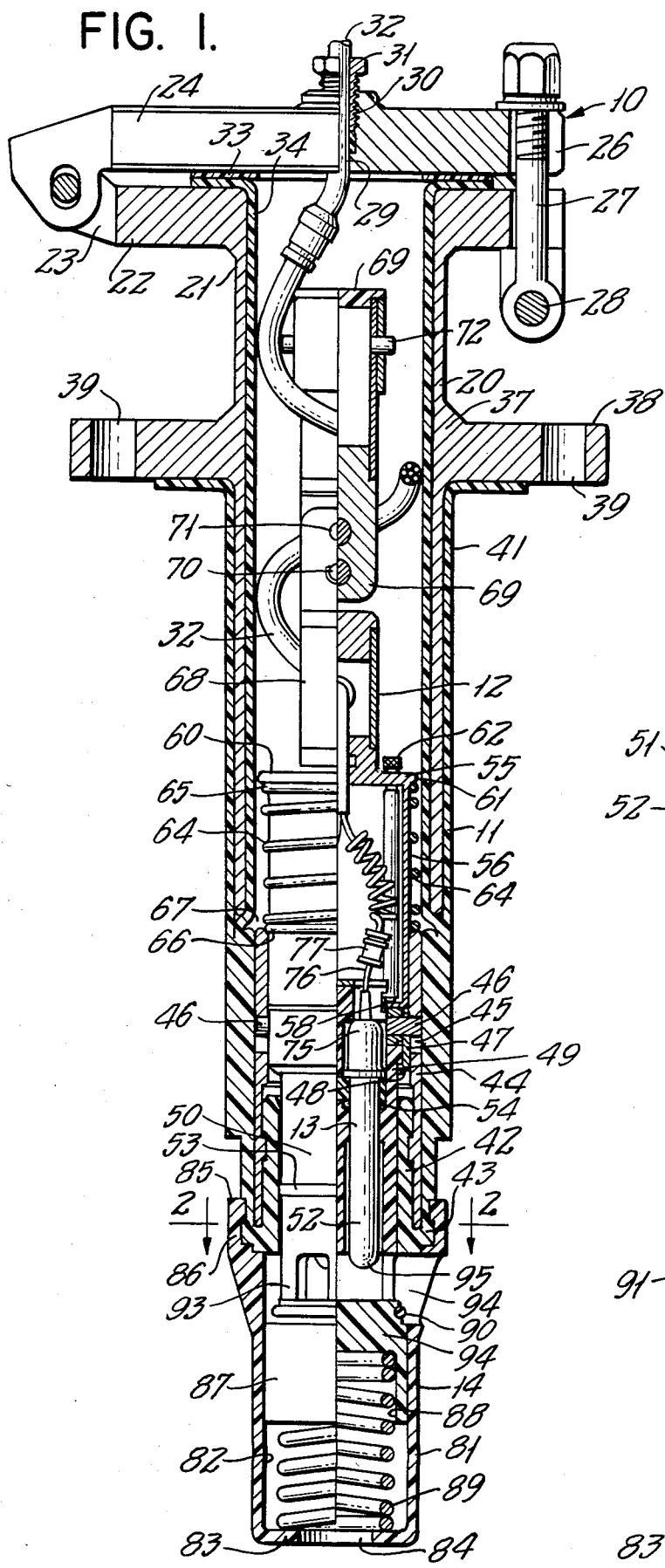
FIG. 1 is a view in elevation, partly in section, of an embodiment of the invention.
Figure 2:
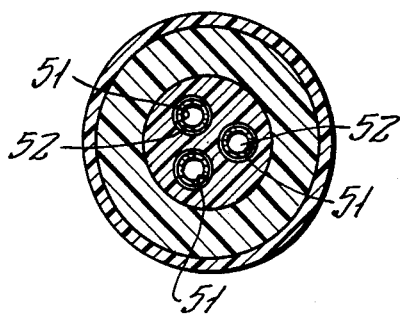
FIG. 2 is a transversed sectional view thereof as seen from the plane 2—2 in FIG. 1.

In accordance with the invention, the device, generally indicated by reference character 10, comprises broadly: a permanently mounted dip tube element 11, a removable probe support element 12, one or more probe elements 13, and an automatic closure element 14.

The dip tube element 11 is preferably formed of metal, and is protectively covered with polytetrafluoroethylene on those surfaces which are inserted into a reactor vessel (not shown). It includes an elongated tubular body 20, an outer end 21, of which is provided with a transversely extending flange 22 forming hinge means 23 supporting a pivotally mounted cover member 24. Opposite the hinged end of the cover member is a slot 26 accommodating a swing bolt 27 pivotally mounted on a pin 28 also carried by the flange 22. The cover member 24 includes a through opening 29 provided with a packing seal 30 held in position by a hollow seal nut 31 through which an outer end of a wire harness 32 projects. A sealing ring 33 meets with the outer end of a liner 34 to effectively close the outer end of the dip tube element 11.

Disposed at a medial location 37 is a mounting flange 38 having a plurality of annularly arranged bores 39 for the accommodation of nuts and bolts (not shown) permitting the device 10 to be anchored within a dip tube opening in a reactor vessel (not shown). Extending inwardly from the flange 38 is an outer protective covering 41 which extends to a lower end 42 of the element 11 having integrally molded bayonet at mounting means 43 to accommodate the element 14. An insert molded metal sleeve 44 includes bayonet locking means 45 selectively engageable with locking pins 46 on the element 12.

The probe support element 12 is of generally elongated configuration, and includes a lower body member 50 defining generally cylindrically shaped recesses 51 accommodating replaceable probe elements 52. Sealing against the contents of the reactor vessel is accomplished by a "D" ring 53 and an "O" ring 54. A removable cover member 55 is in the form of an elongate shell, and includes a tubular body 56, an inner end of which supports a transverse wall 58 which closes the outer ends of the bores 52. The pins 46 are carried on a separate member 47 having a flange 48 engaging a rabbet 49 on the dip tube element 11. The outer wall 60 of the cover member 55 is provided with a laterally extending flange 61, and is held in position by cover retaining threaded members 62. Surrounding the body 50 is a coil spring 64, the outer end 65 of which engages the flange 61, and the inner end 66 of which bears against a surface 67 so as to provide resilient tension tending to keep the locking pins 46 in position.

Extending from the outer surface of the cover member 55 is an extension tube 68 carrying a hingedly connected member 69 interconnected thereto by a pin 70 and a release pin 71. Extending laterally from the extension 69 are pins 72 conveniently engageable by a bayonet type tool (not shown) which permits the entire support element 12 to be rotated to disengage the bayonet interconnection, and axially withdrawn. In the case of low headroom, the extension 69 may be pivoted laterally once the pin 70 has past the outer end of the dip tube element 11.

The outer end 75 of the probe elements 52 is normally provided with electrical conductors 76 which are interconnected through connector 77 to the wire harness 32 in known manner. During withdrawal of the element 12, the wire harness will be entirely withdrawn, even if less than all of the probes are to be replaced.

Figure 3:
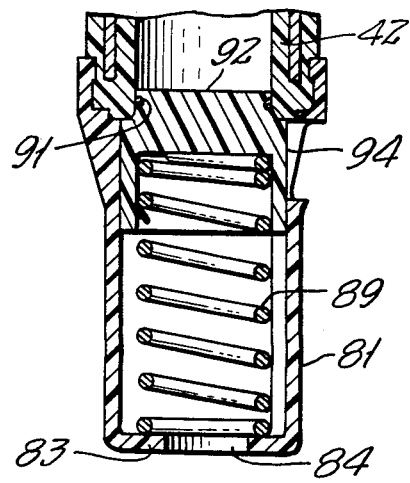
FIG. 3 is a fragmentary view in elevation, partly in section, corresponding to the lower portion of FIG. 1, but showing certain of the parts in altered relative condition.

The automatic closure element 14 is provided for the purpose of effecting an immediate closure to the interior of the reactor vessel upon withdrawal of the probe support element 12. It includes an outer housing 81 having a cylindrical side wall 82 and an outer transverse wall 83 having an opening 84 to permit equalization of pressure at both ends of the valve. The inner end 85 includes corresponding bayonet means 86 for the mounting means 43, so that this element may be periodically replaced if necessary. Disposed within the housing 81 is the valve body 87 having a recess 88 for the accommodation of a protectively covered spring 89. When moved outwardly, an "O" ring 90 cooperates with a seat 91 on the inner end of the dip tube element 11 to effect a seal. An inner transverse surface 92 cooperates with a vented end 93 of the probe support element 12. Comparing the structure of FIG. 1 and FIG. 3, during normal operation, fluid passes through an opening 94 in the side wall 82 to contact the exposed ends 95 of probe elements 52.

Upon removable of the probe support element, the spring 89 expands to move the valve body 87 outwardly to thereby close the opening 94 and bring the "O" ring 90 into engagement with the seat 91 at a point long before the probe support element 12 is removed from the dip tube element 11. While best practice dictates the complete purging of the reactor vessel before attempting to change a probe element, the presence of the element 14 acts as a safety factor should this precaution be omitted.

I wish it to be understood that I do not consider the invention to be limited to the precise details of structure shown and set forth in this specification, for obvious modifications will occur to those skilled in the art to which the invention pertains.

I claim:

1. Improved mounting structure for positioning an electronic probe within a reactor vessel for determining on a substantially continuous basis quantitative values of a desired characteristic of a reaction, comprising: an elongated dip tube element mountable within an opening in said vessel adjacent an outer end thereof, said dip tube element having a centrally disposed bore terminating in an inner end forming a recess; said recess having engageable means; a removable probe carrying element having an outer configuration corresponding to the configuration of said bore in said dip tube element, and having corresponding engageable means on an outer surface thereof selectively cooperating with said engageable means of said dip tube element; said probe carrying element defining at least one cylindrical recess therein corresponding in configuration to the outer cylindrical configuration of an electronic probe; check valve means carried at an inner end of said dip tube element, operative upon disengagement of said probe carrying element therefrom to close said dip tube element against communication with the interior or said reactor vessel; and a means for maintaining said probe within said recess to position an operative end of said probe in exposed condition with said reactor vessel for contact with the contents thereof; said engageable means on said mounting element and said probe carrying element including interacting bayonet pins and grooves; said probe carrying element including a lower body member defining said recess, a probe retaining member overlying said recess, and threaded means retaining said retainer element in position upon said lower body member; a hollow cover member engaging an upper end of said lower body member, said cover member carrying said engageable means on said probe carrying element; said probe carrying element in engaged condition being disposed entirely within said dip tube element, and having a pivotally mounted tool-engaging extension on an outer end thereof to permit effective shortening of the length of said probe carrying element along the axis thereof during withdrawal; said last-mentioned engageable means including at least one laterally-extending pin, said cover member having an end plate thereon, said plate including a laterally-extending flange on the periphery thereof; and a coil spring positioned between said end plate and said pin, a lower end of which contacts a surface of said dip tube element upon engagement of said probe carrying element with said dip tube element to maintain said bayonet pin in engaged condition.

* * * * *